United States Patent [19]

Seyed-Bolorforosh

[11] Patent Number: 5,460,181
[45] Date of Patent: Oct. 24, 1995

[54] ULTRASONIC TRANSDUCER FOR THREE DIMENSIONAL IMAGING

[75] Inventor: Mir S. Seyed-Bolorforosh, Palo Alto, Calif.

[73] Assignee: Hewlett Packard Co., Palo Alto, Calif.

[21] Appl. No.: 319,344

[22] Filed: Oct. 6, 1994

[51] Int. Cl.⁶ .................................................. A61B 8/00
[52] U.S. Cl. ........................... 128/661.01; 128/662.03; 128/916
[58] Field of Search ............... 128/662.03, 661.01, 128/662.06; 310/366, 369; 73/625, 626, 916

[56] References Cited

U.S. PATENT DOCUMENTS

| | | | |
|---|---|---|---|
| 2,589,403 | 3/1952 | Kurie | 171/327 |
| 3,093,760 | 6/1963 | Tarasevich | 310/9.1 |
| 3,378,704 | 4/1968 | Miller et al. | 310/9 |
| 3,401,377 | 9/1968 | Bartlett et al. | 340/173.2 |
| 3,462,746 | 8/1969 | Bartlett | 340/173.2 |
| 3,590,287 | 6/1971 | Berlincourt | 310/8.2 |
| 3,718,898 | 2/1973 | Cook et al. | 340/10 |
| 3,833,825 | 9/1974 | Haan | 310/9.5 |
| 4,062,237 | 12/1977 | Fox | 128/661.01 X |
| 4,087,716 | 5/1978 | Heywang | 310/332 |
| 4,096,756 | 6/1978 | Alphonse | 73/609 |
| 4,211,948 | 7/1980 | Smith et al. | 310/322 |
| 4,356,422 | 10/1982 | van Maanen | 310/322 |
| 4,366,406 | 12/1982 | Smith et al. | 310/334 |
| 4,367,426 | 1/1983 | Kumada et al. | 310/358 |
| 4,672,591 | 6/1987 | Breimesser et al. | 367/152 |
| 4,695,988 | 9/1987 | Banno | 367/154 |
| 4,717,851 | 1/1988 | Fenner et al. | 310/334 |
| 4,736,631 | 4/1988 | Takeuchi et al. | 73/649 |
| 4,835,747 | 5/1989 | Billet | 367/164 |
| 4,939,826 | 7/1990 | Shoup | 310/322 |
| 4,960,107 | 10/1990 | Aida et al. | 601/2 |
| 4,961,424 | 10/1990 | Kubota et al. | 601/2 |
| 5,025,790 | 6/1991 | Dias | 128/662 |

(List continued on next page.)

FOREIGN PATENT DOCUMENTS

| | | | |
|---|---|---|---|
| 0401027 | 12/1990 | European Pat. Off. | B06B 1/06 |
| 3430161A1 | 2/1986 | Germany | G10K 11/02 |
| 45-23667 | 8/1970 | Japan | 310/334 |
| 60-208200 | 10/1985 | Japan | H04R 17/00 |
| 2059716 | 7/1983 | United Kingdom | H04R 17/00 |

OTHER PUBLICATIONS

N. Kim, S. J. Jang, T. R. Shrout; "Relaxor Based Fine Grain Piezoelectric Materials; Proceedings of the 1990 IEEE International Symposium on Applications of Ferroelectrics"; pp. 605–609, 1991.

W. Y. Pan, W. Y. Gu, D. J. Taylor and L. E. Cross; "Large Piezoelectric Effect Induced by Direct Current Bias in PMN:PT Relaxor Ferroelectric Ceramics"; Japanese Journal of Applied Physics, vol. 28, No. 4, 1989, pp. 653–661.

Thomas R. Shrout and Joseph Fielding, Jr.; "Relaxor Ferroelectric Materials"; 1990 Ultrasonic Symposium Proceedings, vol. 2, IEEE, 1990, pp. 711–720.

(List continued on next page.)

*Primary Examiner*—Francis Jaworski
*Attorney, Agent, or Firm*—Jack A. Lenell

[57] ABSTRACT

A method and apparatus for three dimensional ultrasonic scanning with reduced electronic switching and cabling requirements. The invention includes a body including a relaxor ferroelectric ceramic material and electrodes coupled to opposing surfaces of the body. Electronic switches select electrodes so as to select column regions of the body that are arranged adjacent to one another in a row extending radially outward from a central axis of the body. A bias voltage source is coupled with the electronic switches for substantially polarizing ceramic material within the selected column regions of the body. A sector controller dynamically configures the electronic switches to rotationally vary a position of the row arrangement of selected column regions. An oscillating voltage source excites the row of selected column regions to emit an acoustic beam, so that the beam rotationally scans the medium as the sector controller rotationally varies the position of the row arrangement.

21 Claims, 8 Drawing Sheets

U.S. PATENT DOCUMENTS

| | | | |
|---|---|---|---|
| 5,045,746 | 9/1991 | Wersing et al. | 310/334 |
| 5,060,651 | 10/1991 | Kondo et al. | 128/661.01 |
| 5,097,709 | 3/1992 | Masuzawa et al. | 128/661.01 X |
| 5,099,459 | 3/1992 | Smith | 367/153 |
| 5,115,809 | 5/1992 | Saitoh et al. | 128/662 |
| 5,142,187 | 8/1992 | Saito et al. | 310/358 |
| 5,174,296 | 12/1992 | Watanabe et al. | 128/662.03 X |
| 5,175,709 | 12/1992 | Slayton et al. | 367/90 |
| 5,237,542 | 8/1992 | Burke et al. | 367/103 |
| 5,273,045 | 12/1993 | Chihara et al. | 128/661.01 X |

OTHER PUBLICATIONS

Sixte de Fraguier, Jean–Francois Gelly, Leon Volnerman and Olivier Lanuzel; "A Novel Acoustic Design for Dual Frequency Transducers Resulting in Separate Bandpass for Color Flow Mapping (CFM)".

Hiroshi Takeuchi, Hiroshi Masuzawa, and Yukio Ito; "Medical Ultrasonic Probe Using Electrostrictive/Polymer Composite"; 1989 Ultrasonic Symposium Proceedings; IEEE, pp. 705–708.

D. J. Taylor, D. Damjanovic, A. S. Bhalla, and L. E. Cross; "Complex Piezoelectric, Elastic, and Dielectric Coefficient of La–Doped 0.93 $Pb(Mg_{1/3}NB_{2/3})O_3$:0.07 $PbTiO_3$ under DC Bias"; Ferroelectrics Letters, 1990, vol. 11, pp. 1–9.

D. J. Taylor, D. Damjanovic, A. S. Bhalla, and L. E. Cross; "Electric Field Dependence of $d_h$ In Lead Magnesium Niobate.Lead Titanate Ceramics"; Proceedings of the 1990 IEEE International Symposium on Application of Ferroelectric; pp. 341–345, 1991.

Wallace Arden Smith and Bertram A. Auld; "Modeling 1–3 Composite Piezoelectrics: Thickness–Mode Oscillations", IEEE Transactions on Ultrasonics, Ferroelectrics, and Frequency Control, vol. 38, No. 1, Jan., 1991, pp. 40–47.

R. E. Newnham, D. P. Skinner and L. E. Cross; "Connectivity and Piezoelectric–Pyroelectric Composites"; Mat. Res. Bull. vol. 13, pp. 525–536.

Peder C. Pedersen, Oleh Tretiak, and Ping He; "Impedance–Matching Properties of an Inhomogeneous Matching Layer with Continuously Changing Acoustic Impedance"; 1991 Acoustical Society of America, vol. 72, No. 2, pp. 327–336.

Erhard K. Sittig; "Transmission Parameters of Thickness–Driven Piezoelectric Transducers Arranged in Multilayer Configurations"; IEEE Transactions on Sonics and Ultrasonics, vol. SU–14, No. 4, Oct., 1967, pp. 167–174.

Karen Pendergraft and Ronald Piper; "An Exact Solution for a Reflection Coefficient in a medium having an Exponential Impedance profile"; 1993 Acoustical Society of America, vol. 94, No. 1, Jul., 1993. pp. 580–582.

ULTRASONIC TRANSDUCER FOR THREE DIMENSIONAL IMAGING

FIELD OF THE INVENTION

The invention generally relates to ultrasonic imaging and more particularly to three dimensional ultrasonic imaging.

BACKGROUND OF THE INVENTION

Ultrasonic probes provide a convenient and accurate way of gathering information about various structures of interest within a medium under examination by the probe. For example medical ultrasonic probes provide a convenient and accurate way for a physician to collect imaging data of various anatomical parts, such as heart tissue or fetal tissue structures within a patient. It has been discovered that making such imaging data available to surgeons allows otherwise risky surgical procedures to be performed safely. Furthermore, since physicians can now make treatment decisions from results of ultrasound imaging, unnecessary exploratory surgery can be avoided. This has been proven to save money and reduce risks to patients.

In operation, such ultrasonic probes generate a beam of acoustic signals, which is transmitted into the patient and is reflected by various anatomical parts within the patient. The beam is focussed at various depths within the patient and is scanned vertically and horizontally so that the reflected acoustic signals provide three dimensional image data about the various anatomical parts within the patient. The reflected signals are received, analyzed, and processed to produce an image display that is representative of the anatomical parts of the patient.

Early ultrasonic probes were mechanically scanned in one or two dimensions. While such early probes provided some advantages, mechanically scanning could be done at only a limited rate. Furthermore, because a single acoustic lens provided an acoustic beam focussed at only one depth within the patient, such early probes did not provide three dimensional image data at various depths within the patient.

More recent ultrasonic probes provide features such as electronic beam steering and electronic focussing, by using beam forming channels to control amplitude and phasing of a two dimensional array of piezoelectric ceramic transducer elements. Electronic beam steering provides beam scanning at a rate that is much faster than that which is possible with mechanical scanning. Furthermore, electronic focussing provides a flexible way of focussing the acoustic beam at various depths within the patient. Accordingly, such two dimensional arrays provide three dimensional ultrasonic imaging capabilities.

In a typical array of the prior art, each acoustic signal channel requires a respective one piezoelectric ceramic transducer element of the array coupled with a respective one beam forming channel through a respective one signal cable. A large number acoustic signal channels is desirable to provide high resolution acoustic imaging. Accordingly, previously known arrays included a large number of separate piezoelectric ceramic transducer elements, a large number of signal cables, and a large number of beam forming channels to provide high resolution acoustic imaging.

While features such as high resolution acoustic imaging, electronic beam steering, and electronic focussing provide many advantages, two dimensional arrays of the prior art that provide such features are typically difficult and expensive to construct because of a large number of elements, beam forming channels, and cables that are used. For example, in accordance with some teachings of the prior, to provide a high acoustic imaging resolution corresponding to a large number, $N^2$, of acoustic signal channels, requires an array of a large number, $N^2$, of separate piezoelectric ceramic transducer elements, a large number, $N^2$, of signal cables, and a large number, $N^2$, of beam forming channels. Therefore, according to some teachings of the prior art, high acoustic imaging resolution of a 128 by 128 array of piezoelectric ceramic transducer elements 16,384 signal cables and a set of 16,384 beam forming channels. Such large numbers of signal cables and beam forming channels greatly increases the size, cost, and complexity of an acoustic imaging system.

Typically, the signal cables are bound together in a bundle of cables that extends between a probe head and a base station. Ideally, the bundle of cables would be light, thin, flexible, and easy to handle. However as the number of array elements is increased to provide the large number of acoustic signal channels, a number of control cables of the bundle also increases, so that the bundle of cables becomes heavy, thick, bulky, expensive, and more difficult to handle.

What is needed is a new probe having a reduced number of beam forming channels and signal cables, while still providing high resolution acoustic imaging.

SUMMARY OF THE INVENTION

The present invention provides a probe having a reduced number of beam forming channels and signal cables, while still providing high resolution acoustic imaging.

Ultrasonic probes of the prior art included an array of a large number of separate piezoelectric ceramic transducer elements, a large number of signal cables, and a large number of beam forming channels to provide high resolution acoustic imaging. In contrast to the piezoelectric ceramic transducer elements of the prior art which each have a fixed polarization, the present invention uses a probe body including relaxor ferroelectric ceramic material which becomes polarized and therefore electromechanically active only under influence of an applied bias voltage. Instead of using a large number piezoelectric ceramic elements as in the prior art, the present invention provides high resolution acoustic imaging by using column regions of the probe body which are electrically selected by substantially polarizing the regions only when a bias voltage is applied to the regions by a novel electrode arrangement.

In accordance with some teachings of the prior art, to provide a high acoustic imaging resolution corresponding to a large number, $N^2$, of acoustic signal channels, requires an array of a large number, $N^2$, of separate piezoelectric ceramic transducer elements, a large number, $N^2$, of signal cables, and a large number, $N^2$, of beam forming channels. Therefore, according to some teachings of the prior art, high acoustic imaging resolution of a 128 by 128 array of piezoelectric ceramic transducer elements requires 16,384 signal cables and a set of 16,384 beam forming channels.

In contrast, the present invention provides high resolution acoustic imaging equivalent to that which corresponds to a large number, $N^2$, of separate piezoelectric ceramic elements of the prior art, while using a lesser number, N, of signal cables, and a lesser number, N, of beam forming channels. For example, the present invention provides high resolution acoustic imaging equivalent to that which corresponds to a 128 by 128 two dimensional array of piezoelectric ceramic transducer elements of the prior art, while using a lesser number of signal cables (128 cables), and a lesser number of beam forming channels (128 channels).

Briefly, and in general terms, the invention comprises a probe body including a relaxor ferroelectric ceramic material, wherein the body has a first surface, an opposing surface and a central axis. Preferably, the body comprises a composite of the relaxor ferroelectric ceramic material and a filler material. A first set of substantially planar electrodes is electrically coupled with the first surface of the body and is arranged so that each member of the first set of electrodes extends radially outward from the central axis of the body. A second set of substantially planar electrodes is electrically coupled with the opposing surface of the body.

Preferably, each member of the first set of electrodes is substantially sector shaped. Preferably, the second set of electrodes are concentrically arranged about the central axis of the body and each member of the second set of electrodes is substantially semicircular.

The electrodes are electrically coupled with a plurality of column regions of the body. The invention further includes electronic switches for selecting electrodes so as to select column regions of the body that are arranged adjacent to one another in a row extending radially outward from the central axis. A bias voltage source is coupled with the electronic switches for substantially polarizing ceramic material within the selected column regions of the body, while ceramic material in remainder regions of the body is substantially unpolarized. A sector controller dynamically configures the electronic switches to rotationally vary a position of the row arrangement of selected column regions about the central axis of the body while the body remains substantially stationary. An oscillating voltage source excites the row of selected column regions to emit an acoustic beam, so that the beam rotationally scans the medium as the sector controller rotationally varies the position of the row arrangement of selected column regions. The invention further includes a beam forming means for variably phasing respective oscillating voltages coupled with each of the selected regions so that the acoustic beam scans the medium along a radial dimension of the body.

Other aspects and advantages of the present invention will become apparent from the following detailed description, taken in conjunction with the accompanying drawings, illustrating by way of example the principles of the invention.

DETAILED DESCRIPTION OF PREFERRED EMBODIMENT

Figure 1:
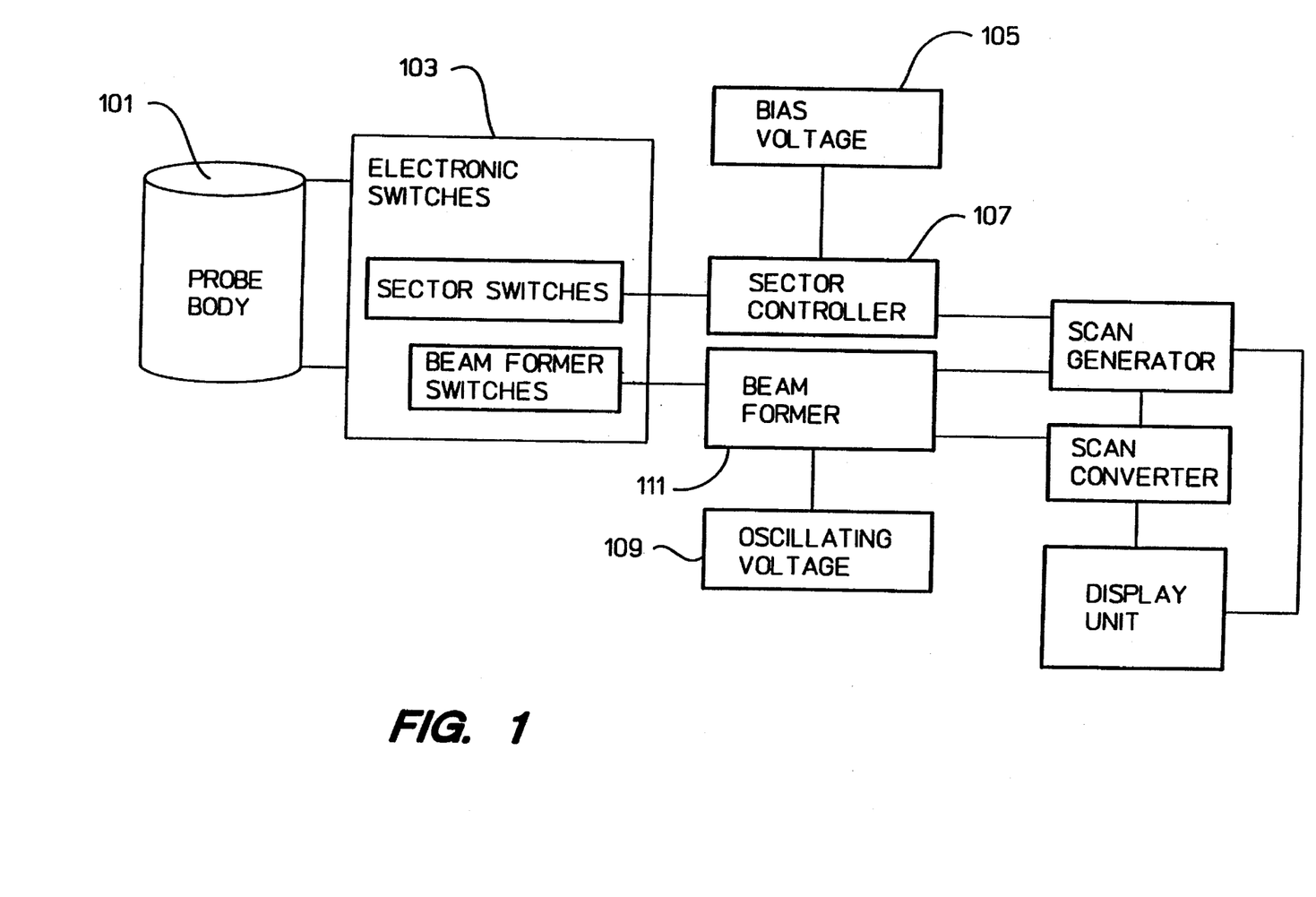
FIG. 1 is a schematic diagram of the invention.

As schematically shown in FIG. 1, the invention includes a probe body 101. The body includes a relaxor ferroelectric ceramic material. Preferably, the relaxor ferroelectric ceramic is a modified relaxor ferroelectric ceramic, doped to have a Curie temperature within a range of zero degrees celsius to sixty degrees celsius. Such doped relaxor ferroelectric ceramics are preferred because they advantageously provide a relatively high dielectric constant while providing a desirable Curie temperature that is near a typical room temperature of twenty five degrees Celsius. Accordingly, relaxor ferroelectric ceramics having a Curie temperature within a range of approximately 25 degrees celsius to approximately 40 degrees celsius are particularly desirable.

Various doped or "modified" relaxor ferroelectric ceramics are known, such as those discussed in "Relaxor Ferroelectric Materials" by Shrout et al., Proceedings of 1990 Ultrasonic Symposium, pp. 711–720, and in "Large Piezoelectric Effect Induced by Direct Current Bias in PMN; PT Relaxor Ferroelectric Ceramics" by Pan et al., Japanese Journal of Applied Physics, Vol. 28, No. 4, April 1989, pp. 653–661. Because these articles provide helpful supportive teachings, they are incorporated herein by reference. A doped or "modified" relaxor such as modified Lead Magnesium Niobate, $Pb(Mg_{1/3}Nb_{2/3})O_3$-$PbTiO_3$, also known as modified PMN or PMN—PT, is preferred. However, other relaxor ferroelectric ceramics such as Lead Lanthanum Zirconate Titanate, PLZT, may be used with beneficial results.

FIG. 2 of the Shrout article is particularly helpful since it shows a phase diagram having a desired pseudo-cubic region for particular mole (x) PT concentrations and particular Curie temperatures of a $(1-x)Pb(Mg_{1/3}Nb_{2/3})O_3$-$(x)PbTiO_3$ solid solution system. FIG. 8 of the Shrout article is also particularly helpful since it shows dielectric constant and Curie temperature of various alternative compositionally modified PMN ceramics. Among these alternatives, those doped with $Sc^{+3}$, $Zn^{+2}$, or $Cd^{+2}$ and having a Curie temperature within a range of approximately zero degrees Celsius to approximately sixty degrees Celsius are preferred.

Preferably, the body comprises a composite of the relaxor ferroelectric ceramic material and a filler material, such as polyethylene, for substantially acoustically isolating the selected regions from one another. While the relaxor ferroelectric ceramic material has a dielectric constant, preferably the filler material has a dielectric constant substantially lower than that of the ceramic material for substantially electrically isolating each of the selected regions from one another.

As will be discussed in further detail later herein, a first set of substantially planar electrodes is electrically coupled with a first surface of the body and is arranged so that each member of the first set of electrodes extends radially outward from a central axis of the body. A second set of substantially planar electrodes is electrically coupled with an opposing surface of the body. The electrodes are electrically coupled with a plurality of column regions of the body.

As shown in FIG. 1 the invention further includes electronic switches 103 for selecting electrodes so as to select column regions of the body that are arranged adjacent to one another in a row extending radially outward from the central axis. The electronic switches include sector switches as well as beam forming switches. A quasi-static (DC) bias voltage source 105 is coupled with the electronic switches for substantially polarizing ceramic material within the selected column regions of the body, while ceramic material in remainder regions of the body is substantially unpolarized. A sector controller 107 dynamically configures the electronic switches to rotationally vary a position of the row arrangement of selected column regions about a central axis of the body while the body remains substantially stationary.

An oscillating voltage source 109 excites the row of selected column regions to emit an acoustic beam, so that the beam rotationally scans the medium as the sector controller rotationally varies the position of the row arrangement of selected column regions. A beam former 111 for variably phasing respective oscillating voltages is coupled with each of the selected regions so that the acoustic beam scans the medium along a radial dimension of the body. The beam former also provides electronic focussing of the acoustic beam at various depths.

Operation of the sector controller and the beam former are co-ordinated by a scan generator coupled thereto as shown in FIG. 1. A scan converter including data memory blocks configured for storing three dimensional imaging data is coupled to the beam former and the scan generator. A display unit is coupled to the scan converter for displaying a high resolution acoustic image.

Figure 2A:
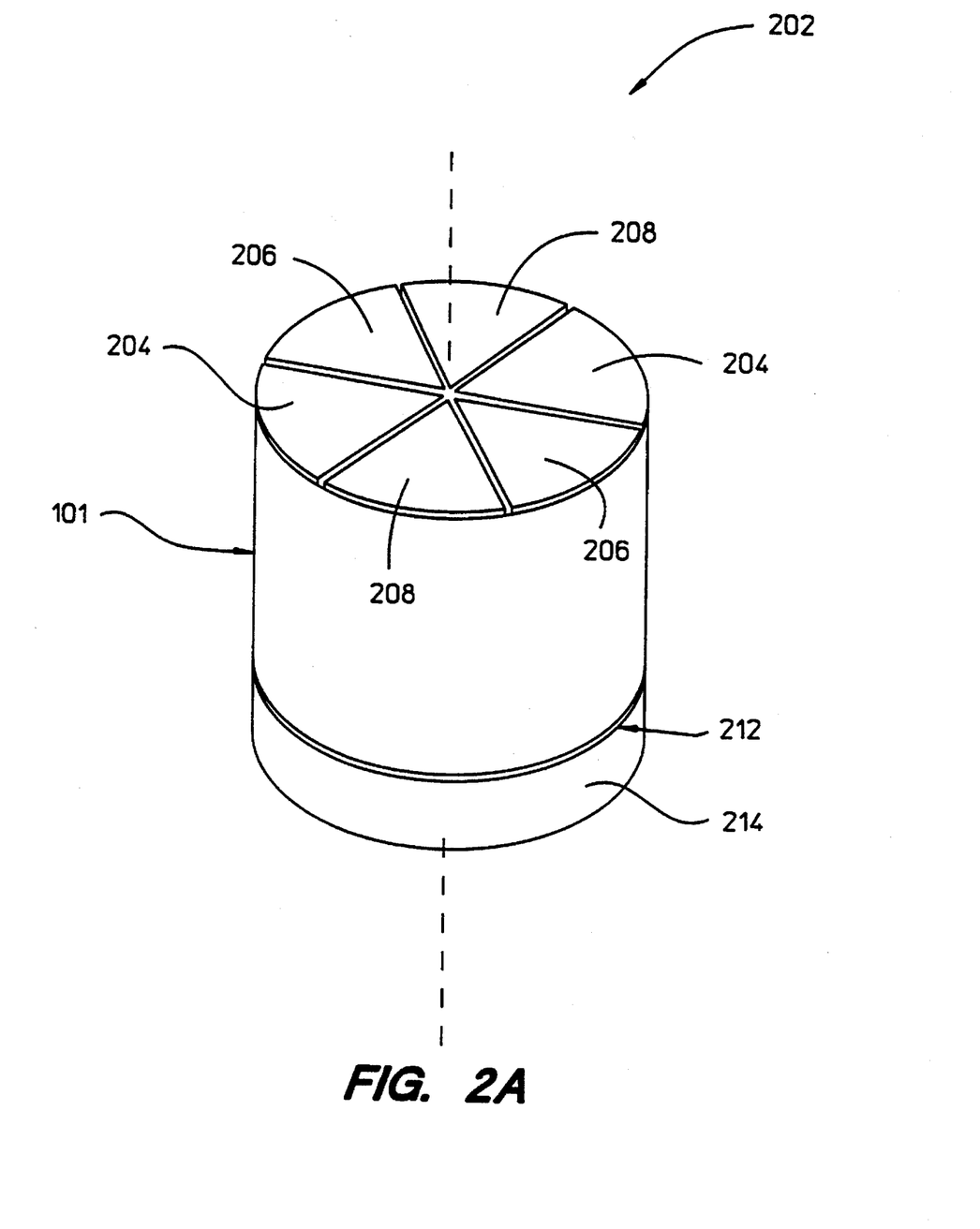
FIGS. 2A and 2B are each views of a probe body of the schematic diagram of FIG. 1.

FIG. 2A is a simplified view showing the probe body 111. As shown, the body has a first surface, an opposing surface and a central axis. A first set of substantially planar electrodes 202 is electrically coupled with the first surface of the body and is arranged so that each member of the first set of electrodes extends radially outward from the central axis of the body. Preferably, each member of the first set of electrodes is substantially sector shaped as shown in FIG. 2A. For example, as shown in FIG. 2A, the first set of electrodes includes six sector shaped electrodes. In particular, a first pair 204 of members of the first set of electrodes are aligned on opposing sides of the central axis and are preferably electrically coupled together. Additionally a second pair 206 of members of the first set of electrodes are also aligned on opposing sides of the central axis and are preferably electrically coupled together. Furthermore, a third pair 208 of members of the first set of electrodes are also aligned on opposing sides of the central axis and are preferably electrically coupled together.

A second set of substantially planar electrodes 212 is electrically coupled with the opposing surface of the body. As shown, in the preferred embodiment the second set of electrodes is sandwiched between the probe body and an acoustically absorbing backing layer 214, preferably made from epoxy. A preferred way of making the first and second set of electrodes is by suitably masking the probe body and sputtering metal onto the probe body.

Figure 2B:
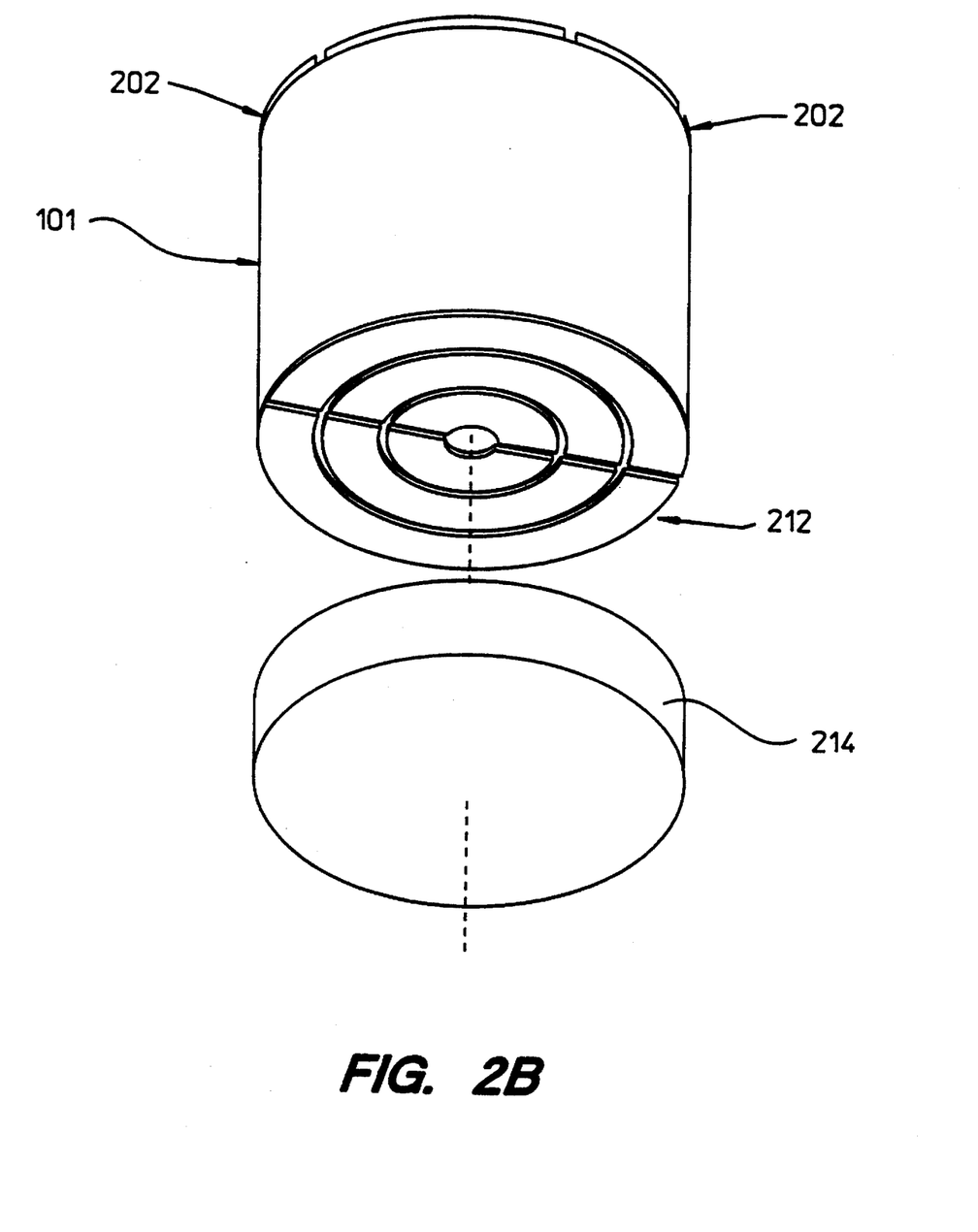

FIG. 2B is a simplified exploded view revealing the second set of electrodes, which are concentrically arranged about the central axis of the body. Preferably each member of the second set of electrodes is substantially semicircular. For example, as shown in FIG. 2B the second set of electrodes includes six semicircular electrodes.

While the first and second set of electrodes of the invention are substantially planar, it should be understood that they need not be strictly flat since the electrodes in alternative embodiments of the invention have surfaces that are otherwise configured, for example as curved surfaces, provide beneficial results. Furthermore, it should be understood that while the preferred embodiment includes a larger number of electrodes than are shown in the figures, for the sake of simplicity, fewer electrodes are shown in the figures. For example, while for the sake of simplicity FIGS. 2A and 2B show three pairs of radial electrodes and six semicircular electrodes, it should be understood that an exemplary preferred embodiment includes 128 pairs of radial electrodes and 128 semicircular electrodes. This exemplary preferred embodiment of the invention provides high resolution acoustic imaging equivalent to that which corresponds to a 128 by 128 two dimensional array of piezoelectric ceramic transducer elements of the prior art, while using a relatively small number of signal cables (128 cables) coupled to the semicircular electrodes, and a relatively small number of beam forming channels (128 channels).

Figure 3A:
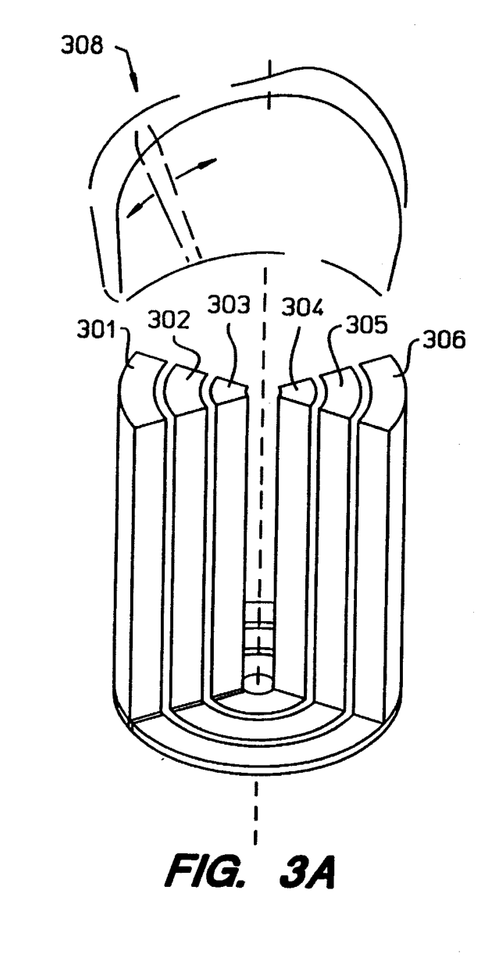
FIGS. 3A, 3B, and 3C are cut away views of the probe body shown in FIGS. 2A and 2B illustrating operation of invention.
Figure 3B:
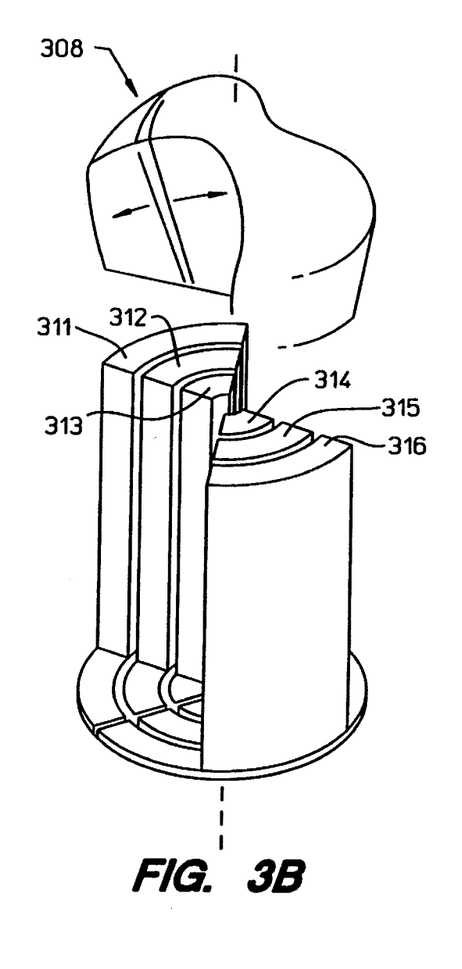
Figure 3C:
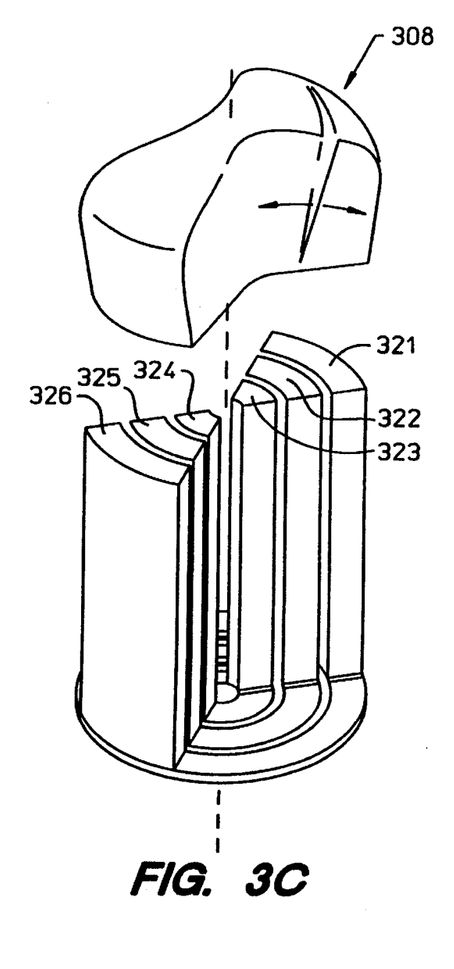

The relaxor ferroelectric ceramic material becomes polarized and therefore electromechanically active only under influence of the applied bias voltage. The present invention provides a large number of acoustic signal channels by using column regions of the body which are electrically selected by substantially polarizing the regions only when a bias voltage is applied to the regions by the novel electrode arrangement discussed previously herein and illustrated in FIGS. 2A and 2B. FIGS. 3A, 3B, and 3C are cut away views of the probe body shown in FIGS. 2A and 2B illustrating operation of invention.

The electronic switches select the first pair of members of the first set of electrodes, so as to select column regions 301,302, 303, 304, 305,306 of the body that are arranged adjacent to one another in a row extending radially outward from the central axis as shown in FIG. 3A. The bias voltage source coupled with the electronic switches substantially polarizes ceramic material within the selected column regions of the body, while ceramic material in remainder regions of the body is substantially unpolarized. In FIG. 3A the substantially unpolarized regions of the body and the first set of electrodes are cut away to reveal the substantially polarized selected column regions.

The oscillating voltage source excites the row of selected column regions to emit an acoustic beam 308. Of course the acoustic beam is invisible. However, for the sake of illustration, the acoustic beam has been representatively drawn as shown in FIG. 3A. The beam former variably phases respective oscillating voltages coupled with each of the selected regions so that the acoustic beam scans a medium under examination by the probe along a radial dimension of the probe body as shown in FIG. 3A. For the sake of simplicity, the medium under examination by the probe is not shown in the figures.

As illustrated by FIGS. 3A, 3B, and 3C, the controller dynamically configures the electronic switches to rotationally vary a position of the row arrangement of selected column regions about the central axis of the body while the body remains substantially stationary. The oscillating voltage source excites the row of selected column regions to emit an acoustic beam, so that the beam rotationally scans the medium under examination by the probe as the controller rotationally varies the position of the row arrangement of selected column regions.

For example, as shown in FIG. 3B, the electronic switches select the second pair of members of the first set of electrodes by applying a quasi-static (DC) bias voltage thereto, so as to select column regions 311,312, 313, 314, 315, 316 of the body that are once again arranged adjacent to one another in a row extending radially outward from the central axis. The row arrangement shown in FIG. 3B is rotated with respect to the row arrangement shown in FIG. 3A. Once again, the bias voltage source coupled with the electronic switches substantially polarizes ceramic material within selected column regions of the body, while ceramic material in remainder regions of the body is substantially unpolarized. Just as in FIG. 3A, in FIG. 3B the substantially unpolarized regions of the body and the first set of electrodes are cut away to reveal the substantially polarized selected column regions.

As shown in FIG. 3C, the electronic switches select the third pair of members of the first set of electrodes, so as to select column regions 321, 322, 323, 324, 325, 326 of the body that are once again arranged adjacent to one another in a row extending radially outward from the central axis. The row arrangement shown in FIG. 3C is once again rotated with respect to the row arrangements shown in FIGS. 3A and 3B. Once again, the bias voltage source coupled with the electronic switches substantially polarizes ceramic material within the selected column regions of the body, while ceramic material in remainder regions of the body is substantially unpolarized. Just as in FIG. 3A and 3B, in FIG. 3C the substantially unpolarized regions of the body and the first set of electrodes are cut away to reveal the substantially polarized selected column regions.

Figure 4:
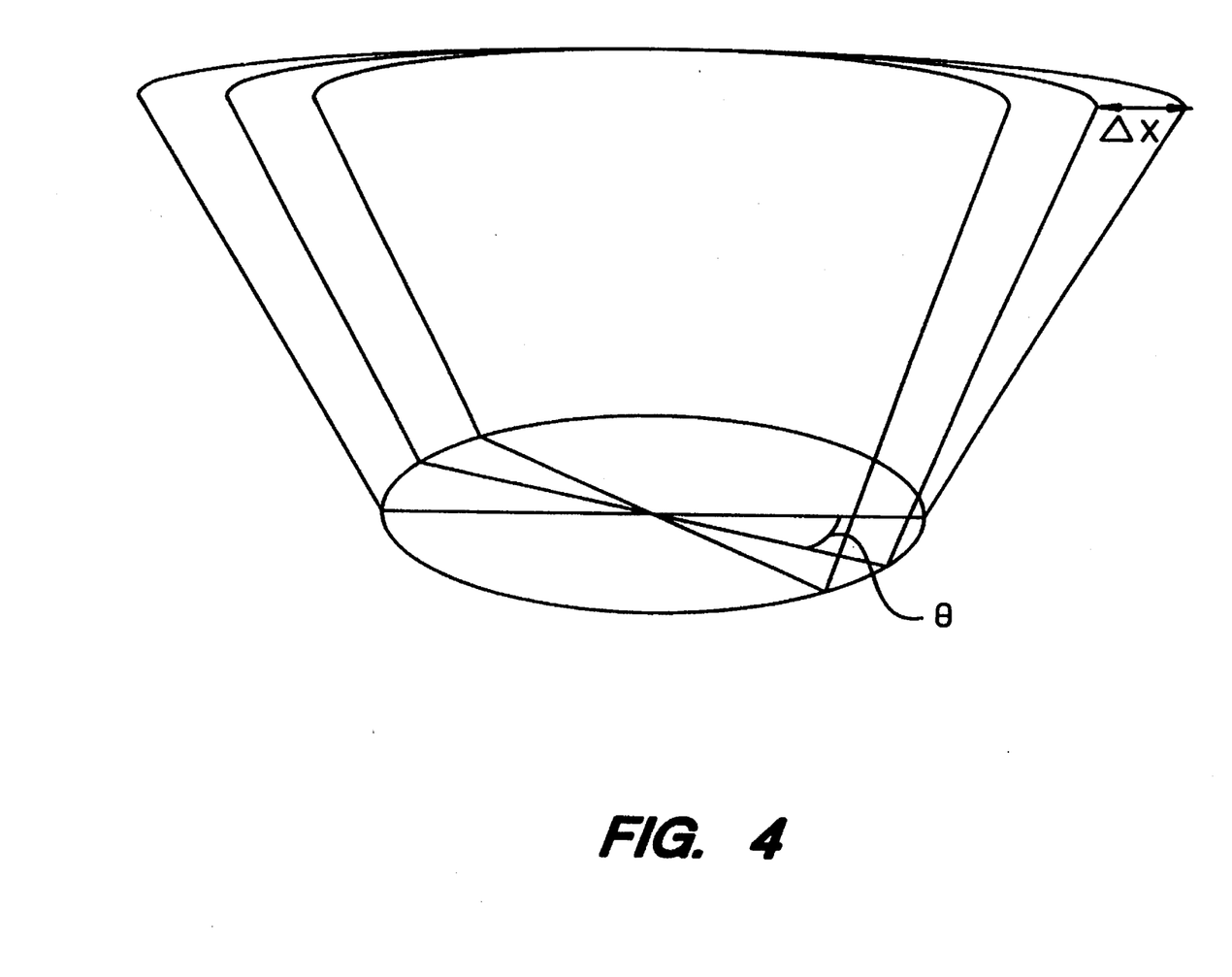
FIG. 4 is an alternative depiction of an acoustic beam shown in FIGS. 3A, 3B, and 3C.

FIG. 4 is an alternative depiction of an acoustic beam shown in FIGS. 3A, 3B, and 3C. As shown the acoustic beam is substantially fan shaped, and rotates though an angle, theta, and is radially scanned an amount, delta X.

Figure 5:
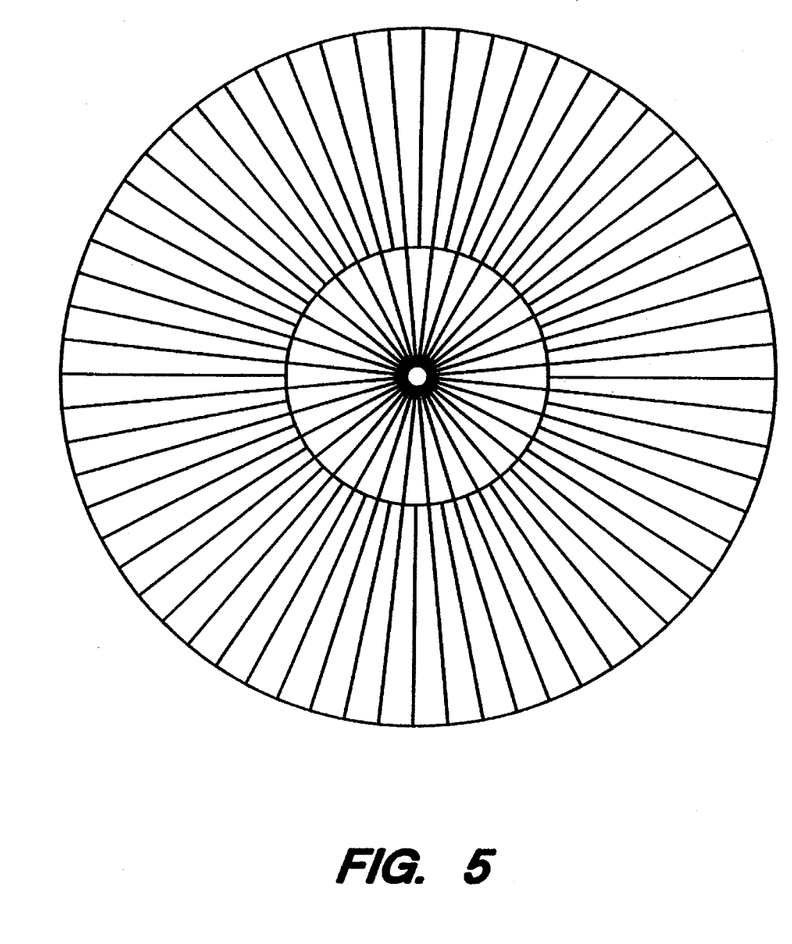
FIG. 5 is a plan view of an alternative embodiment of radial electrodes of the invention.

FIG. 5 is a plan view of an alternative embodiment of radial electrodes of the invention. As show, the radial electrodes of the alternative embodiment include a central grouping of radial electrodes and a peripheral grouping of sector electrodes. The central grouping of radial electrodes advantageously provide greater central imaging resolution. For each member of the central grouping of radial electrodes, two images are obtained from each adjacent member of the peripheral grouping of radial electrodes.

Figure 6:
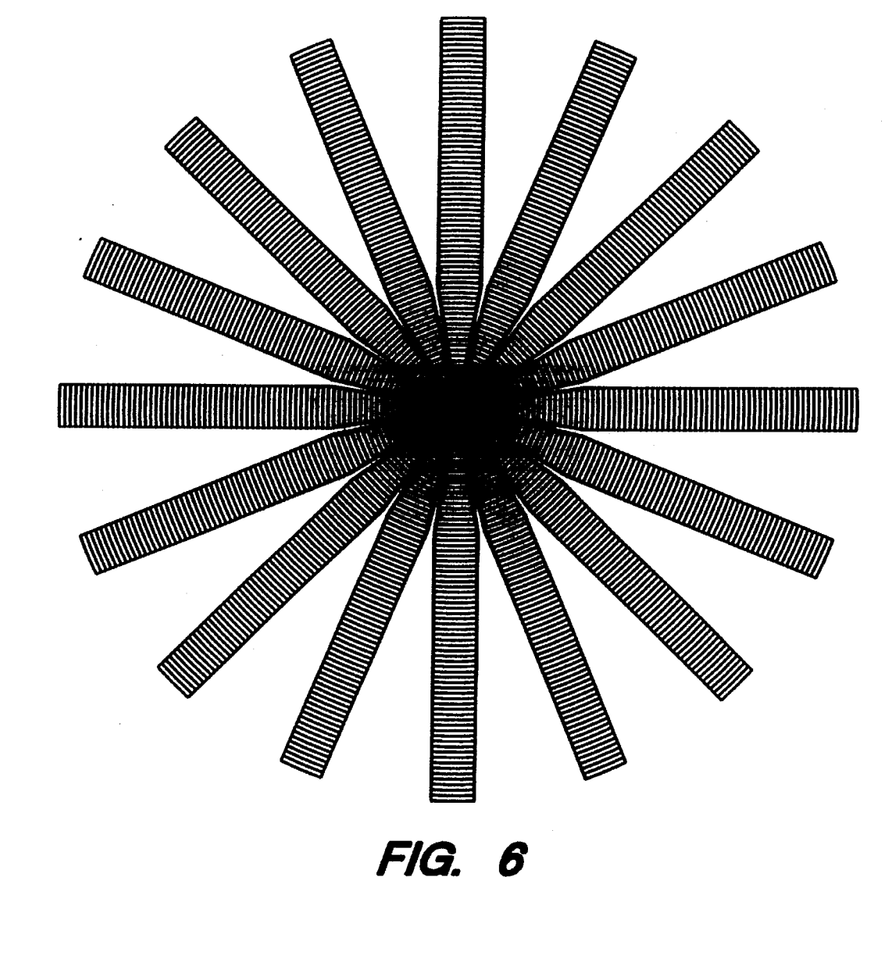
FIG. 6 is a plan view of another alternative embodiment of radial electrodes of the invention.

FIG. 6 is a plan view of another alternative embodiment of radial electrodes of the invention. As shown the electrodes a substantially sector shaped, but are truncated so that a portion of each electrode is generally rectangular.

Figure 7:
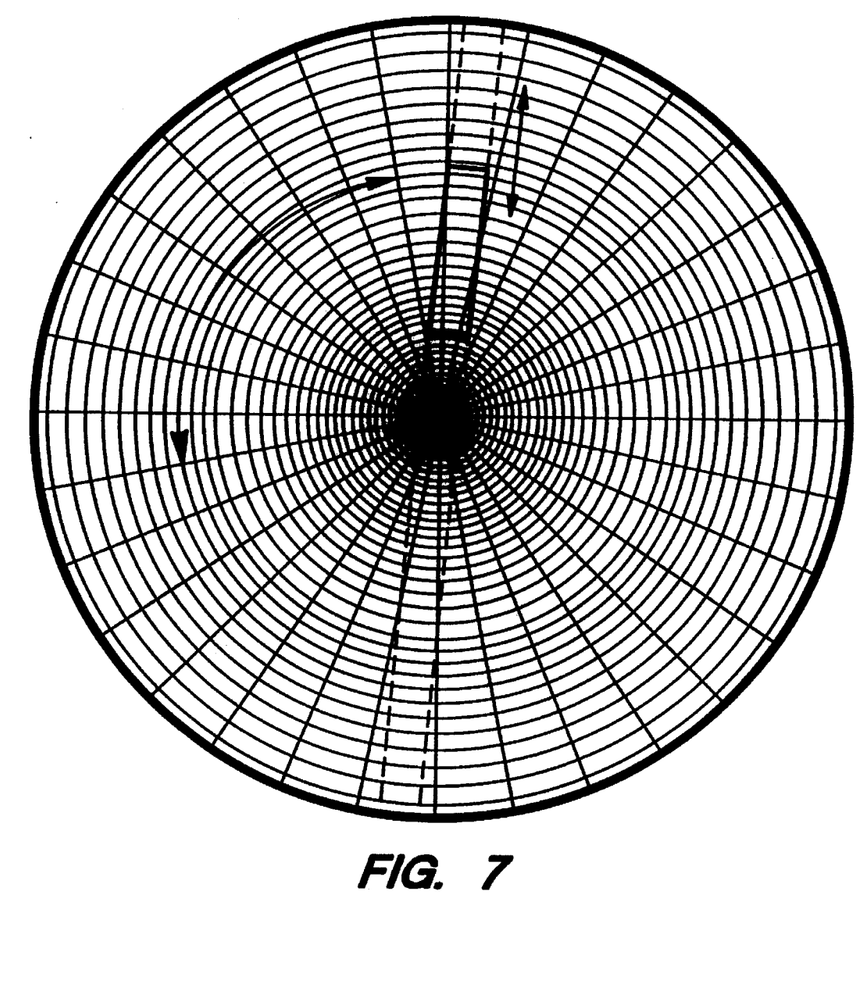
FIG. 7 is a diagram illustrating yet another alternative embodiment of the invention.

FIG. 7 is a diagram illustrating yet another alternative embodiment of the invention. As representatively shown, a rectangular acoustic aperture combining signals of a plurality of selected column regions is radially scanned across a face of the probe body. Once a linear walk is complete, the rectangular acoustic aperture is rotationally shifted about the central axis of the probe body, and the radial scan of the aperture is repeated.

The method and apparatus of the invention provide three dimensional ultrasonic scanning with reduced electronic switching and cabling requirements. Although specific embodiments of the invention have been described and illustrated, the invention is not to be limited to the specific forms or arrangements of parts so described and illustrate, and various modifications and changes can be made without departing from the scope and spirit of the invention. Within the scope of the appended claims, therefore, the invention may be practiced otherwise than as specifically described and illustrated.

What is claimed is:

1. An apparatus comprising:
   a body including a relaxor ferroelectric ceramic material, the body having a first surface, an opposing surface and a central axis;
   a first set of substantially planar electrodes electrically coupled with the first surface of the body, wherein each member of the first set of electrodes extends radially outward from the central axis of the body; and
   a second set of substantially planar electrodes electrically coupled with the opposing surface of the body; wherein members of the second set of electrodes are concentrically arranged about the central axis of the body.

2. An ultrasonic probe as in claim 1 wherein each member of the second set of electrodes is substantially semicircular.

3. An ultrasonic probe as in claim 1 wherein the second set of electrodes include substantially semicircular concentric electrodes.

4. An ultrasonic probe as in claim 1 wherein the body comprises a composite of a relaxor ferroelectric ceramic material and a filler material.

5. An ultrasonic probe as in claim 4 wherein:
   the relaxor ferroelectric ceramic material has a dielectric constant; and
   the filler material has a dielectric constant substantially lower than that of the ceramic material.

6. A method comprising:
   providing a body having a central axis, said body including relaxor ferroelectric ceramic material;
   selecting column regions of the body that are arranged adjacent to one another in a row extending radially outward from the central axis;
   substantially polarizing ceramic material within the selected column regions of the body, while ceramic material in remainder regions of the body is substantially unpolarized;
   rotationally varying a position of the row arrangement of selected column regions about the central axis of the body while the body remains substantially stationary; and
   exciting the row of selected column regions to emit an acoustic beam, so that the beam rotationally scans a medium adjacent to the probe as the position of the row arrangement is rotationally varied.

7. The method of claim 6 further comprising variably phasing respective oscillating voltages coupled with each of the selected regions so that the acoustic beam scans the medium along a radial dimension of the body.

8. The method of claim 6 further comprising:
   combining signals of a plurality of selected column regions to provide a rectangular acoustic aperture; and
   radially scanning the acoustic aperture across a face of the probe body.

9. An ultrasonic probe for examining a medium comprising:
   a body including relaxor ferroelectric ceramic material, the body having a central axis;
   electrodes electrically coupled with a plurality of column regions of the body;
   electronic switches for selecting electrodes so as to select column regions of the body that are arranged adjacent to one another in a row extending radially outward from the central axis;
   a bias voltage source coupled with the electronic switches for substantially polarizing ceramic material within the selected column regions of the body, while ceramic material in remainder regions of the body is substantially unpolarized;
   a sector controller for dynamically configuring the electronic switches to rotationally vary a position of the row arrangement of selected column regions about the central axis of the body while the body remains substantially stationary; and
   an oscillating voltage source for exciting the row of selected column regions to emit an acoustic beam, so that the beam rotationally scans the medium as the sector controller rotationally varies the position of the row arrangement of selected column regions.

10. An ultrasonic probe as in claim 9 wherein:

the body including relaxor ferroelectric ceramic material has a radial dimension; and the probe further comprises a means for variably phasing respective oscillating voltages coupled with each of the selected regions so that the acoustic beam scans the medium along the radial dimension of the body.

11. An ultrasonic probe as in claim 9 wherein the electrodes include:

a first set of substantially planar electrodes electrically coupled with a first surface of the body; and a second set of substantially planar electrodes electrically coupled with an opposing surface of the body.

12. An ultrasonic probe as in claim 11 wherein each member of the first set of electrodes extends radially outward from the central axis of the body.

13. An ultrasonic probe as in claim 11 wherein each member of the first set of electrodes is substantially sector shaped.

14. An ultrasonic probe as in claim 11 wherein members of the second set of electrodes are concentrically arranged about the central axis of the body.

15. An ultrasonic probe as in claim 11 wherein each member of the second set of electrodes is substantially semicircular.

16. An ultrasonic probe as in claim 11 wherein the second set of electrodes include substantially semicircular concentric electrodes.

17. An ultrasonic probe as in claim 11 wherein the first set of electrodes include a central grouping of radial electrodes and a peripheral grouping of radial electrodes.

18. An ultrasonic probe as in claim 11 wherein each member of the first set of electrodes is substantially sector shaped and is truncated so that a portion of each electrode is generally rectangular.

19. An ultrasonic probe as in claim 9 wherein the body comprises a composite of the relaxor ferroelectric ceramic material and a filler material for substantially acoustically isolating the selected regions from one another.

20. An ultrasonic probe as in claim 9 wherein:

the relaxor ferroelectric ceramic material has a dielectric constant; and the body comprises:

a composite of the relaxor ferroelectric ceramic material; and a filler material having a dielectric constant substantially lower than that of the ceramic material for substantially electrically isolating each of the selected regions from one another.

21. An apparatus comprising:

a body including a relaxor ferroelectric ceramic material, the body having a first surface, an opposing surface and a central axis;

a first set of substantially planar electrodes electrically coupled with the first surface of the body, wherein each member of the first set of electrodes extends radially outward from the central axis of the body and wherein each member of the first set of electrodes is substantially sector shaped; and a second set of substantially planar electrodes electrically coupled with the opposing surface of the body.

* * * * *